United States Patent [19]

Haga et al.

[11] Patent Number: 4,608,080
[45] Date of Patent: Aug. 26, 1986

[54] HERBICIDAL 2-PHENYL-4,5,6,7-TETRAHYDRO-2H-INDAZOLES

[75] Inventors: Toru Haga, Takarazuka; Eiki Nagano, Nishinomiya; Ryo Sato, Toyonaka; Ryo Yoshida, Kawanishi, all of Japan

[73] Assignee: Sumitomo Chemical Company, Limited, Osaka, Japan

[21] Appl. No.: 731,784

[22] Filed: May 8, 1985

[30] Foreign Application Priority Data

May 18, 1984 [JP] Japan ................. 59-101341

[51] Int. Cl.$^4$ ............... A01N 43/56; C07D 231/56
[52] U.S. Cl. ..................................... 71/92; 548/369
[58] Field of Search .......................... 548/369; 71/92

[56] References Cited

U.S. PATENT DOCUMENTS 4,059,434 11/1977 Wolf .................. 548/369

OTHER PUBLICATIONS

Morrison and Boyd, *Organic Chemistry*, 4th edit., 1983, pp. 208–211.

*Primary Examiner*—Richard A. Schwartz
*Assistant Examiner*—Kurt G. Briscoe
*Attorney, Agent, or Firm*—Birch, Stewart, Kolasch & Birch

[57] ABSTRACT

A compound of the formula:

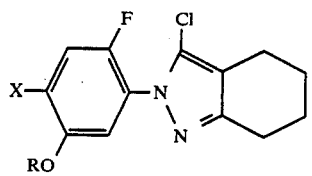

wherein R is a mono- or di-halo($C_3$–$C_4$)alkenyl group or a mono-halo($C_3$–$C_4$)alkynyl group and X is a chlorine atom or a bromine atom, which is useful as a herbicide.

7 Claims, No Drawings

HERBICIDAL 2-PHENYL-4,5,6,7-TETRAHYDRO-2H-INDAZOLES

The present invention relates to 2-phenyl-4,5,6,7-tetrahydro-2H-indazoles (hereinafter referred to as "2-phenyltetrahydroindazole(s)"), and their production and use.

The 2-phenyltetrahydroindazoles are represented by the formula:

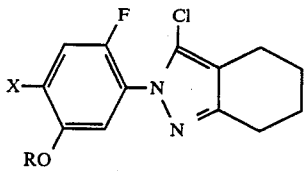
(I)

wherein R is a mono- or di-halo($C_3$–$C_4$)alkenyl group or a mono-halo($C_3$–$C_4$)alkynyl group and X is a chlorine atom or a bromine atom.

It is known that certain kinds of 2-phenyl-4,5,6,7-tetrahydro-2H-indazoles are effective as herbicides. For instance, the herbicidal use of 3-chloro-2-(2,4-dichloro-5-methoxyphenyl-4,5,6,7-tetrahydro-2H-indazole is disclosed in U.S. Pat. No. 4,059,434. However, their herbicidal effect is not necessarily satisfactory.

It has been found that the 2-phenyltetrahydroindazoles (I) exhibit a strong herbicidal activity against a wide variety of weeds including broad-leaved weeds and Graminaceous weeds in agricultural plowed field by foliar or soil treatment and do not produce any material phytotoxicity on various agricultural crops (i.e. corn, wheat, soybean). Examples of broad-leaved weeds are common lambsquarters (*Chenopodium album*), slender amaranth (*Amaranthus gracilis*), radish (*Raphanus sativus*), hemp sesbania (*Sesbania exaltata*), sicklepod (*Cassia obtusifolia*), velvetleaf (*Abutilon theophrasti*), prickly sida (*Sida spinosa*), tall morningglory (*Ipomoea purpurea*), jimsonweed (*Datura stramonium*), black nightshade (*Solanum nigrum*), common cocklebur (*Xanthium strumarium*), common sunflower (*Helianthus annuus*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), oat (*Avena sativa*), etc.

Particularly notable is that the 2-phenyltetrahydroindazoles (I) exert a high herbicidal activity against paddy field weeds including Graminaceous weeds such as barnyardgrass (*Echinochloa oryzicola*), broad-leaved weed such as common falsepimpernel (*Lindernia procumbens*), indian toothcup (*Rotala indica*) and waterwort (*Elatine triandra*), Cyperaceous weeds such as hardstem bulrush (*Scirpus juncoides*) and needle spikerush (*Eleocharis acicularis*), and arrowhead (*Sagittaria pygmaea*) without any phytotoxicity to rice plants on flooding treatment. Their selectivity to rice plants in paddy fields on flooding treatment is quite excellent.

Accordingly, the 2-phenyltetrahydroindazoles (I) can be used as herbicides applicable to agricultural plowed fields as well as paddy fields.

The 2-phenyltetrahydroindazole (I) is obtained by reacting a compound of the formula:

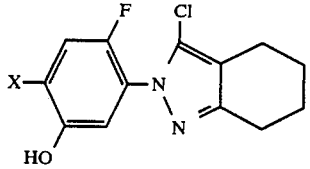
(II)

wherein X is as defined above with a compound of the formula:

R-Y (III)

wherein R is as defined above and Y is an acid residue such as a chlorine atom, a bromine atom, an iodine atom, a methanesulfonyloxy group or a p-toluenesulfonyloxy group in an inert solvent in the presence of an acid-eliminating agent, if necessary, with a phase transfer catalyst, at a temperature of 20° to 150° C. for a period of 1 to 24 hours.

The compound (III), the acid-eliminating agent and the phase transfer catalyst may be used respectively in amounts of 1 to 10 equivalents, 1 to 10 equivalents and 0.01 to 0.1 equivalent to 1 equivalent of the compound (II).

Examples of the inert solvent are aliphatic hydrocarbons (e.g. hexane, heptane, ligroin), aromatic hydrocarbons (e.g. benzene, toluene, xylene), ethers (e.g. diisopropyl ether, dioxane, ethyleneglycol dimethyl ether), sulfur compounds (e.g. dimethylsulfoxide, sulfolane), water, and their mixtures.

As the acid-eliminating agent, there may be used basic substances such as inorganic bases (e.g. sodium hydroxide, potassium hydroxide, sodium carbonate, potassium carbonate, sodium hydride). Examples of the phase transfer catalyst are tri-n-butylbenzylammonium chloride, tetra-n-butylammonium bromide, etc.

The reaction mixture is usually subjected to post-treatment such as extraction with a solvent and concentration. When desired, the recovered product may be purified by a per se conventional procedure such as column chromatography.

Practical and presently preferred embodiments of the production of the 2-phenyltetrahydroindazoles (I) are illustratively shown in the following example.

EXAMPLE 1

3-Chloro-2-(4-chloro-2-fluoro-5-hydroxyphenyl)-4,5,6,7-tetrahydro-2H-indazole (1 g) was suspended in a solution of potassium hydroxide (0.84 g) in water (8 ml). Dimethylsulfoxide (21 ml) was added to the suspension to make a uniform solution. To the resultant solution, 1,3-dichloro-1-butene (1.26 g) was added, and the mixture was stirred at 100° C. for 4 hours. After being allowed to cool, water was added to the mixture, which was then extracted with ethyl acetate. The organic layer was washed with water, dried and concentrated. The residue was purified by silica gel thin chromatography using a mixture of ether and hexane (1:3) as an eluent to give 3-chloro-2-[4-chloro-2-fluoro-5-(3-chloro-2-propenyloxy)phenyl]-4,5,6,7-tetrahydro-2H-indazole (0.65 g) (Compound No. 2). M.P., 68.5°–70.5° C.

Examples of the 2-phenyltetrahydroindazole (I) produced in the same manner as above are shown in Table 1.

TABLE 1

(I) Structure: phenyl ring with F, Cl, X, and OR substituents, connected via N to a tetrahydroindazole ring system.

| Compound No. | X | R | Physical property |
|---|---|---|---|
| 1 | Cl | CH₂=C(Cl)—CH₂— | M.P. 112–113° C. |
| 2 | Cl | ClCH=CH—CH₂— | M.P. 68.5–70.5° C. |
| 3 | Cl | (Cl)(Cl)C=CH—CH₂— | M.P. 74.2° C. |
| 4 | Cl | ClCH₂CH=CH—CH₂— | M.P. 106.4° C. |
| 5 | Cl | BrCH₂CH=CH—CH₂— | M.P. 135.7° C. |
| 6 | Br | (Cl)(Cl)C=CH—CH₂— | M.P. 112.2° C. |
| 7 | Cl | Cl—C≡C—CH₂— | M.P. 132.9° C. |
| 8 | Cl | Br—C≡C—CH₂— | M.P. 154.5° C. |

In the practical use of the 2-phenyltetrahydroindazoles (I), they may be applied in any preparation form such as emulsifiable concentrates, wettable powders, suspensions, granules, etc. in combination with conventional solid or liquid carriers or diluents as well as surface active agents or auxiliary agents.

The content of the 2-phenyltetrahydroindazole (I) as the active ingredient in such a formulation is usually within a range of 0.03 to 90% by weight, preferably of 0.05 to 80% by weight.

Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc.

The surface active agent used for emulsification, dispersion or spreading may be any kind of anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts are by weight.

The compound number of the active ingredient corresponds to the one in Table 1.

FORMULATION EXAMPLE 1

Fifty parts of Compound No. 2, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Ten parts of Compound No. 1, 14 parts of polyoxyethylenestyrylphenyl ether, 6 parts of calcium dodecylbenzenesulfonate, 30 parts of xylene and 40 parts of isophorone are well mixed while being powdered to obtain an emulsifiable concentrate.

FORMULATION EXAMPLE 3

0.1 Part of Compound No. 1, 0.9 part of synthetic hydrous silicate, 2 parts of calcium ligninsulfonate, 30 parts of bentonite and 67 parts of kaolin clay are well mixed while being powdered. The mixture is then kneaded with water, granulated and dried to obtain granules.

FORMULATION EXAMPLE 4

Twenty-five parts of Compound No. 2 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

The 2-phenyltetrahydroindazoles (I) thus formulated in any suitable formulation are useful for the pre-emergence or post-emergence control of undesired weeds by soil or foliar treatment as well as flood fallowing treatment. These treatments include application to the soil surface prior to or after the transplanting or the incorporation into the soil. The foliar treatment may be effected by spraying the herbicidal composition containing the 2-phenyltetrahydroindazoles (I) over the top of the plants. It may also be applied directly to the weeds if care is taken to keep the chemical off the crop foliage.

The 2-phenyltetrahydroindazoles (I) of the present invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the 2-phenyltetrahydroindazoles (I) can be used as herbicides applicable to agricultural plowed fields as well as paddy fields. They are also useful as herbicides to be employed for orchard, pasture land, lawn, forest, non-agricultural field, etc.

The dosage rate of the 2-phenyltetrahydroindazoles (I) may vary on prevailing weather conditions, formulation used, prevailing season, mode of application, soil involved, crop and weed species, etc. Generally, however, the dosage rate is from 0.02 to 100 grams, preferably from 0.04 to 40 grams, of the active ingredient per are. The herbicidal composition of the invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the 2-phenyltetrahydroindazoles (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 2 below were used for comparison.

TABLE 2

| Compound No. | Chemical structure | Remarks |
|---|---|---|
| A | [structure with Cl, Cl, Cl, H₃CO, N–N, cyclohexene fused] | U.S. Pat. No. 4,059,434 |
| B | [structure: Cl, Cl, Cl-phenyl-O-phenyl-NO₂] | Commercially available herbicide; "chloronitrofen" |
| C | [structure with F, Cl, Cl, HC≡CCH₂O, N–N, cyclohexene fused] | EP-A-0105721 |

TEST EXAMPLE 1

Cylindrical plastic pots (diameter, 10 cm; height, 10 cm) were filled with upland field soil, and the seeds of Japanese millet, tall morningglory and velvetleaf were sowed therein and covered with soil. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 3.

TABLE 3

| Compound No. | Dosage (g/are) | Herbicidal activity | | |
|---|---|---|---|---|
| | | Japanese millet | Tall morning-glory | Velvet-leaf |
| 1 | 20 | 5 | 5 | 5 |
| | 10 | 5 | 5 | 5 |
| 2 | 20 | 5 | 5 | 5 |
| | 10 | 5 | 5 | 5 |
| 3 | 20 | 5 | 5 | 5 |
| | 10 | 4 | 4 | 5 |
| 4 | 20 | 5 | 4 | 5 |
| | 10 | 4 | 3 | 5 |
| 5 | 20 | 5 | 4 | 5 |

TABLE 3-continued

| Compound No. | Dosage (g/are) | Herbicidal activity | | |
|---|---|---|---|---|
| | | Japanese millet | Tall morning-glory | Velvet-leaf |
| | 10 | 4 | 3 | 5 |
| 6 | 20 | 5 | 5 | 5 |
| | 10 | 4 | 4 | 5 |
| 7 | 20 | 5 | 5 | 5 |
| | 10 | 4 | 4 | 5 |
| B | 20 | 2 | 2 | 3 |
| | 10 | 1 | 0 | 2 |

TEST EXAMPLE 2

Cylindrical plastic pots (diameter, 10 cm; height, 10 cm) were filled with upland field soil, and the seeds of Japanese millet, oats, radish and velvetleaf were sowed therein and cultivated in a greenhouse for 10 days. A designated amount of the test compound formulated in an emulsifiable concentrate according to Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 4.

TABLE 4

| Compound No. | Dosage (g/are) | Herbicidal activity | | | |
|---|---|---|---|---|---|
| | | Japanese millet | Oats | Radish | Velvet-leaf |
| 1 | 5 | 5 | 5 | 5 | 5 |
| | 2.5 | 5 | 5 | 5 | 5 |
| 2 | 5 | 5 | 5 | 5 | 5 |
| 3 | 5 | 5 | 5 | 5 | 5 |
| | 2.5 | 5 | 4 | 5 | 5 |
| 5 | 5 | 5 | 5 | 5 | 5 |
| | 2.5 | 4 | 4 | 5 | 5 |
| 7 | 5 | 5 | 5 | 5 | 5 |
| | 2.5 | 5 | 4 | 5 | 5 |
| 8 | 5 | 4 | 4 | 5 | 5 |
| B | 5 | 2 | 0 | 0 | 3 |
| | 2.5 | 0 | 0 | 0 | 1 |

TEST EXAMPLE 3

Cylindrical plastic pots (diameter, 8 cm; height, 12 cm) were filled with paddy field soil, and the seeds of barnyardgrass (*Echinochloa oryzicola*) and broad-leaved weeds (e.g. common falsepimpernel, indian toothcup, waterwort) were sowed in 1 to 2 cm depth. Water was poured therein to make a flooded condition, and rice seedlings of the 2-leaf stage were transplanted therein and grown in a greenhouse. Six days (at that time the weeds began to germinate) thereafter, a designated amount of the test compound formulated in an emulsifiable concentrate according to Formulation Example 2 and diluted with water (5 ml) was applied to the pots by perfusion. The test plants were grown for further 20 days in the greenhouse, and the herbicidal activity was examined. The results are shown in Table 5.

TABLE 5

| Compound No. | Dosage (g/are) | Herbicidal activity | | |
|---|---|---|---|---|
| | | Rice plant | Barnyard-grass | Broad-leaved weeds |
| 1 | 0.32 | 1 | 5 | 5 |
| | 0.16 | 0 | 5 | 5 |
| 2 | 0.32 | 1 | 5 | 5 |
| 3 | 0.32 | 1 | 4 | 5 |

TABLE 5-continued

| Compound No. | Dosage (g/are) | Herbicidal activity | | |
|---|---|---|---|---|
| | | Rice plant | Barnyard-grass | Broad-leaved weeds |
| | 0.16 | 0 | 4 | 5 |
| 7 | 0.32 | 1 | 5 | 5 |
| | 0.16 | 1 | 4 | 5 |
| B | 0.32 | 0 | 0 | 0 |

TEST EXAMPLE 4

Wagner's pots (1/5000 are) were filled with paddy field soil, and the seeds of barnyardgrass (*Echinochloa oryzicola*), broad-leaved weeds (e.g. common falsepimpernel, indian toothcup, waterwort) and hardstem bulrush and the statoblast of needle spikerush were sowed in 1 to 2 cm depth. Water was poured therein to make a flooded condition. Rice seedlings of the 2.5-leaf stage were transplanted therein and grown in a greenhouse. Six days (at that time barnyardgrass started to germinate) thereafter, a designated amount of the test compound formulated in an emulsifiable concentrate according to Formulation Example 2 and diluted with water (10 ml) was applied to the pots by perfusion, followed by addition of water thereto to make a 4 cm depth. The test plants were grown for further 20 days in the greenhouse, and the herbicidal activity was examined. The results are shown in Table 6.

TABLE 6

| Compound No. | Dosage (g/are) | Herbicidal activity | | | |
|---|---|---|---|---|---|
| | | Rice plant | Barn-yard-grass | Broad-leaved weeds | Needle spikerush | Hardstem bulrush |
| 1 | 0.08 | 0 | 5 | 5 | 5 | 4 |
| | 0.04 | 0 | 5 | 5 | 4 | — |
| 3 | 0.16 | 1 | 5 | 5 | 4 | 5 |
| | 0.08 | 0 | 4 | 5 | — | 4 |
| 7 | 0.16 | 1 | 5 | 5 | 5 | 5 |
| | 0.08 | 0 | 4 | 5 | — | 4 |
| A | 0.08 | 0 | 1 | 3 | 2 | 0 |
| | 0.04 | 0 | 0 | 1 | 0 | 0 |

TEST EXAMPLE 5

Wagner's pots (1/5000 are) were filled with paddy field soil, and the seeds of barnyardgrass (*Echinochloa oryzicola*), broad-leaved weeds (e.g. common falsepimpernel, indian toothcup, waterwort) and hardstem bulrush and the statoblast of needle spikerush were sowed in 1 to 2 cm depth. Water was poured therein to make a flooded condition. Rich seedlings of the 2.5-leaf stage were transplanted therein and grown in a greenhouse. Thirteen days (at that time barnyardgrass grew to 2-leaf stage) thereafter, a designated amount of the test compound formulated in an emulsifiable concentrate according to the Formulation Example 2 and diluted with water (10 ml) was applied to the pots by perfusion, followed by addition of water thereto to make a 4 cm depth. The test plants were grown for further 20 days in the greenhouse, and the herbicidal activity was examined. The results are shown in Table 7.

TABLE 7

| Compound No. | Dosage (g/are) | Herbicidal activity | | | | |
|---|---|---|---|---|---|---|
| | | Rice plant | Barn-yard-grass | Broad-leaved weeds | Needle spikerush | Hardstem bulrush |
| 1 | 0.16 | 0 | 5 | 5 | 5 | 3 |
| | 0.08 | 0 | 4 | 5 | 4 | — |
| A | 0.16 | 0 | 0 | 3 | 2 | 0 |
| | 0.08 | 0 | 0 | 1 | 0 | 0 |

TEST EXAMPLE 6

Vats (33 cm × 23 cm × 11 cm) were filled with upland field soil, and the seeds of soybean, tall morningglory, velvetleaf, hemp sesbania, black nightshade, common lambsquarters, slender amaranth, green foxtail and barnyardgrass (*Echinochloa cruss-galli*) were sowed therein to 1 to 2 cm depth. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 8.

TABLE 8

| Compound No. | Dosage (g/are) | Herbicidal activity | | | | | | | | |
|---|---|---|---|---|---|---|---|---|---|---|
| | | Soybean | Tall morning-glory | Velvet-leaf | Hemp sesbania | Black night-shade | Common lambs-quarters | Slender amaranth | Green fox-tail | Barnyard-grass |
| 1 | 5 | 1 | 5 | 5 | 5 | 5 | 5 | 5 | 5 | 5 |
| | 2.5 | 0 | 5 | 5 | 5 | 5 | 5 | 5 | 5 | 5 |
| B | 5 | 0 | 0 | 1 | 0 | 1 | 1 | 1 | 0 | 1 |
| | 2.5 | 0 | 0 | 0 | 0 | 0 | 0 | 0 | 0 | 0 |

TEST EXAMPLE 7

Vats (33 cm × 23 cm × 11 cm) were filled with upland field soil and the seeds of soybean, corn, tall morningglory, velvetleaf, black nightshade and redroot pigweed were sowed therein. Cultivation was carried out in a greenhouse. A designated amount of the test compound formulated in an emulsifiable concentrate according to Formulation Example 2 and diluted with water containing a spreading agent was sprayed to the foliage of the test plants over the top by means of a small hand sprayer at a spray volume of 5 liters per are. Thereafter, the test plants were further grown in the greenhouse for 30 days, and the herbicidal activity and the phytotoxicity were examined. At the time of the application, the growing stage of the test plants varied depending on their species; weeds and corn were generally at the 1 to 4 leaf stage and in 2 to 12 cm height, while soybean was at the 0.5 leaf stage. The results are shown in Table 9.

TABLE 9

| Compound No. | Dosage (g/are) | Herbicidal activity | | | | | |
|---|---|---|---|---|---|---|---|
| | | Soybean | Corn | Tall morning-glory | Velvet-leaf | Black night-shade | Redroot pig-weed |
| 1 | 0.04 | 1 | 0 | 4 | 5 | 5 | 5 |
| 3 | 0.16 | 1 | 1 | 4 | 5 | 5 | 5 |
| | 0.04 | 1 | 1 | 3 | 5 | 5 | 4 |

TABLE 9-continued

| | | Herbicidal activity | | | | | |
|---|---|---|---|---|---|---|---|
| Compound No. | Dosage (g/are) | Soybean | Corn | Tall morning-glory | Velvet-leaf | Black night-shade | Red-root pig-weed |
| 7 | 0.04 | 1 | 1 | — | 5 | 4 | 4 |
| C | 0.16 | 5 | 1 | 5 | 5 | 5 | 5 |
|   | 0.04 | 4 | 1 | 4 | 5 | 5 | 5 |
|   | 0.01 | 2 | 0 | 2 | 4 | 4 | 3 |

What is claimed is:

1. A compound of the formula:

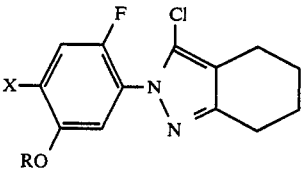

wherein R is a mono- or di-halo($C_3$–$C_4$)alkenyl group or a mono-halo($C_3$–$C_4$)alkynyl group and X is a chlorine atom or a bromine atom.

2. The compound according to claim 3, which is 3-chloro-2-[4-chloro-2-fluoro-5-(3-chloro-2-propenyloxy)-phenyl]-4,5,6,7-tetrahydro-2H-indazole.

3. The compound according to claim 1, wherein R contains a chlorine or bromine atom.

4. A herbicidal composition which comprises as an active ingredient a herbicidally effective amount of the compound according to claim 1, and an inert carrier or diluent.

5. A method for controlling weeds which comprises applying a herbicidally effective amount of the compound according to claim 1 to the area where weeds grow or will grow.

6. The method according to claim 5, wherein the area is the paddy field of rice plant.

7. The method according to claim 5, wherein the area is the field of soybean or corn.

* * * * *